United States Patent [19]

Down

[11] 4,255,963
[45] Mar. 17, 1981

[54] HYDROGEN METER FOR LIQUID LITHIUM

[75] Inventor: Michael G. Down, Plum Boro, Pa.

[73] Assignee: Westinghouse Electric Corp., Pittsburgh, Pa.

[21] Appl. No.: 11,831

[22] Filed: Feb. 13, 1979

[51] Int. Cl.³ ............................................. G01N 7/10
[52] U.S. Cl. ......................................... 73/19; 55/158
[58] Field of Search ............................... 73/19; 55/158

[56] References Cited

U.S. PATENT DOCUMENTS

| | | | |
|---|---|---|---|
| 3,350,846 | 11/1967 | Makrides | 55/158 |
| 3,977,232 | 8/1976 | Hickam | 73/19 |

*Primary Examiner*—S. Clement Swisher
*Attorney, Agent, or Firm*—M. P. Lynch

[57] ABSTRACT

A niobium or vanadium membrane, which resists lithium corrosion and exhibits significant hydrogen permeation at temperatures of about 500° C. or higher, is employed in a membrane/meter device for measuring the hydrogen in a lithium/hydrogen solution.

4 Claims, 2 Drawing Figures

HYDROGEN METER FOR LIQUID LITHIUM

BACKGROUND OF THE INVENTION

Conventional hydrogen meters for use with liquid sodium employ a thin, probe-type nickel diffusion membrane which is immersed in the liquid metal. Hydrogen from the sodium diffuses through the membrane and enters an internal vacuum chamber where it is measured by an ion pump current. The current is a direct function of the hydrogen flux through the membrane and therefore an indication of the hydrogen concentration in the sodium.

For operation of a similar hydrogen flux device in liquid lithium, there are two fundamental problems to be overcome. First, the nickel membrane material typically employed in hydrogen meters for use with liquid sodium has a considerably higher solubility in lithium than in sodium at the temperature of interest. At 600° C. the value in lithium is 0.01 mol percent nickel, whereas in sodium the corresponding solubility is $2 \times 10^{-5}$ mol percent nickel. In a flowing loop system, such a high solubility would inevitably lead to significant loss of membrane material. Secondly, although dilute solutions of hydrogen in lithium obey Sievert's law, the equilibrium hydrogen pressures generated by such lithium solutions are as many as nine orders of magnitude lower than for corresponding sodium solutions. For this reason the flux produced across a conventional nickel membrane when subjected to a lithium solution would also be considerably lower and probably beyond the measuring capability of a conventional ion pump.

SUMMARY OF THE INVENTION

It has been determined experimentally that by substituting niobium or vanadium as the membrane material, instead of nickel, that the resulting membrane element will exhibit minimum membrane dissolution in highly contaminated lithium liquids, high $H_2$ permeation, and will develop a hydrogen flux significantly higher than that developed by the nickel membrane.

It has been shown that for nickel and sodium, diffusion through the nickel membrane is the rate-controlling step for the transport of hydrogen from the liquid metal solution. Assuming this also to be the case for niobium or vanadium in a lithium/hydrogen solution, the following expression for the theoretical ion pump current can be derived:

$$I = (C_H K_1 K_2 A / K_3 L) \qquad (1)$$

where
- $I$ = ion pump current, $\mu A$
- $A$ = area of membrane, $cm^2$
- $L$ = thickness of membrane, cm
- $K_1$ = Sievert's constant for lithium/hydrogen, $torr^{\frac{1}{2}}$ wppm$^{-1}$
- $K_2$ = permeation coefficient of membrane, $torr^{-\frac{1}{2}}$ $cm^{-1} s^{-1}$
- $K_3$ = ion pump factor, torr-l $s^{-1}$ $\mu A^{-1}$ Therefore, for a given concentration of hydrogen in lithium, the value of the ion current can be maximized by adjusting the above parameters as follows:
(a) a high value of $K_2$
(b) a high value of $K_1$
(c) a high value for $A$
(d) a low value for $L$ The choice of niobium or vanadium as the membrane material for use in lithium/hydrogen solutions produces distinct advantages with respect to items (a) and (d) above thereby partially offsetting the intrinsic low value of $K_1$. It has been shown that the permeation constant for bulk diffusion of hydrogen through niobium is approximately $10^2$ greater than through nickel, thereby markedly enhancing the hydrogen flux. In addition, the superior strength of niobium metal permits significantly thinner membranes than those used in conventional nickeltype meters. This factor results in an increase in the ion pump current.

A further operational advantage that is realized when a niobium membrane is contacted by liquid lithium is that liquid lithium, which is a strong reducing agent, cleans undesirable surface oxides from the niobium membrane. If the surface oxides were permitted to build up, they would restrict hydrogen permeation.

Vanadium likewise exhibits an $H_2$ permeation constant and corrosion resistance characteristic which makes it a desirable membrane material for use in lithium/hydrogen solutions.

An effective hydrogen monitoring device for liquid lithium systems could be employed in fusion reactor systems which will use the liquid metal as coolant and tritium breeding blanket. Such blankets will contain transient high concentrations of hydrogen isotopes and the real-time monitoring of their production and subsequent extraction is important to the viability of such reactors. In addition, the monitoring of small hydrogen increases can be used to detect water to lithium leaks in steam generators for such reactors.

DESCRIPTION OF THE DRAWINGS

The invention will become more readily apparent from the following exemplary description in connection with the accompanying drawings.

DESCRIPTION OF THE PREFERRED EMBODIMENT

The detailed structure and operation of a diffusion-type hydrogen meter for use in liquid sodium is described in U.S. Pat. No. 3,977,232, entitled DIFFUSION-TYPE HYDROGEN METER, issued Aug. 31, 1976, assigned to the assignee of the present invention, and incorporated herein by reference.

Figure 1:
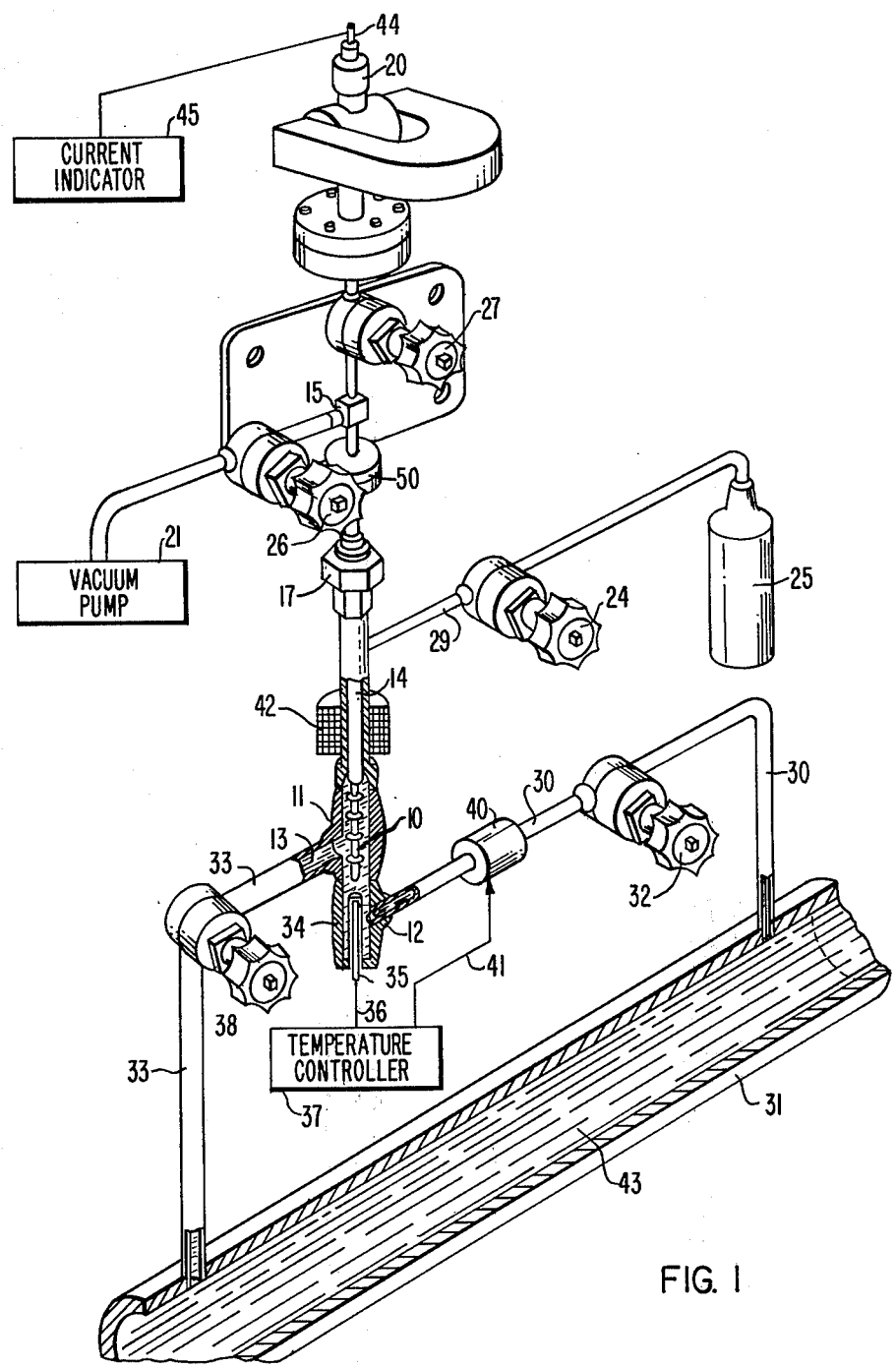
FIG. 1 is a pictorial diagram of a diffusiontype hydrogen meter connected to measure the hydrogen concentration in a lithium/hydrogen solution.

The hydrogen meter pictorially illustrated in FIG. 1 corresponds essentially to that illustrated and described in the above-referenced United States patent, with the critical difference being that the diffusion membrane 10 is niobium or vanadium thus rendering the hydrogen meter suitable for measuring hydrogen in a lithium/hydrogen solution.

While the following discussion documents the unique capability of niobium and vanadium membranes for monitoring hydrogen in lithium/hydrogen solutions, it is recognized that a small percentage of an alloy, such as zirconium, could be added to the niobium or vanadium to further reduce the likelihood of oxide coatings or further enhance the corrosion resistance of the membrane 10.

Referring to FIG. 1, a closed end diffusion tubular membrane 10 of niobium or vanadium is positioned within a housing 11. The housing 11 has two openings 12, 13 which permit liquid lithium to enter the housing 11 and circulate around the membrane 10. The membrane 10 is connected to a tube 14 which is, in turn, secured to the housing 11 by a mounting nut 17. The lower end of the membrane 10 is closed and the membrane 10 and the tube 14 are connected through a T connector 15 to an ion pump 20 and a vacuum pump 21. Three valves 26 and 27 permit the vacuum pump 21 and the ion pump 20 to be selectively coupled to the membrane 10.

The housing 11 has an opening in the upper part thereof which is coupled to a tube 29 and the valve 24 to a supply of compressed argon 25. A portion of the liquid lithium 43 flowing in conduit 31 enters the housing 11 via tube 30 and opening 12, circulates around the membrane 10, through the outlet opening 13 and returns to the conduit 31 via a tube 33. Tubes 30, 33 include valves 32, 38. To change the membrane 10, valves 32, 38 are closed to assure that no lithium flows through the housing 11.

The housing 11 includes a sensor well 34 in the lower end thereof. A temperature sensor 35 is mounted in the sensor well 34 and coupled by a cable 36 to a temperature controller 37. The temperature controller 37 is, in turn, coupled to a heater element 40 by a cable 41. A second heater element 42 is positioned around the upper part of the housing 11.

The system illustrated in FIG. 1 is properly connected to measure the hydrogen content of liquid lithium 43 which flows through the conduit 31. The system is placed in operation by evacuating the interal cavity of the tubular membrane 10 by activating the vacuum pump 21. After the membrane 10 has been evacuated, a cuttoff valve 26 is closed to isolate the vacuum pump 21 from the membrane 10. The ion pump cutoff valve 27 is opened to couple the ion pump to the membrane 10. Liquid lithium is then pumped through conduit 31 such that a portion of the lithium flows through the housing 11 by way of the input tube 30 and the output tube 33.

After the membrane 10 has been evacuated and the ion pump 20 connected to the membrane by opening the ion pump shutoff valve 27, the ion pump 20 is started by coupling a high voltage to the ion pump electrode 44. The hydrogen in the lithium surrounding the membrane 10 diffuses through the membrane 10 and is removed by the ion pump 20. The current in the ion pump has a predetermined relationship to the hydrogen removed from the space enclosed by the tubular membrane 10 in the tube 14. The amount of hydrogen diffusing through the membrane 10 has a predetermined relationship to the concentration of hydrogen in the lithium surrounding membrane 10. Thus, the current in the ion pump 20 is an indication of the hydrogen concentration in the lithium. The ion pump current is measured and displayed on a current indicator 45.

A suitable ion pump is available commercially. A typical pump is Model No. 913-5000, manufactured by Varian Associates.

The rate at which hydrogen diffuses from the lithium through the membrane 10 is a function of the concentration of hydrogen in the lithium and the temperature of the lithium. In order to eliminate the need for a correction for the temperature of the lithium, it is normally preferred to maintain the temperature of the lithium surrounding the membrane 10 constant. In the system of FIG. 1, this is accomplished by positioning a temperature sensor 35 in the sensor well 34 to measure the temperature of the lithium in the vicinity of the membrane 10. The output of the temperature sensor 35 is coupled to a temperature controller 37 which is, in turn, coupled to a heater 40 which is positioned around the lithium input tube 30. The temperature controller 37 and the heater 40 are adjusted to maintain the temperature of the lithium entering the housing 11 substantially constant.

The disclosed system may also be used to measure the hydrogen concentration in lithium vapor. The operation of the meter are substantially the same because lithium, either liquid or vapor, will not diffuse through the membrane 10.

Figure 2:
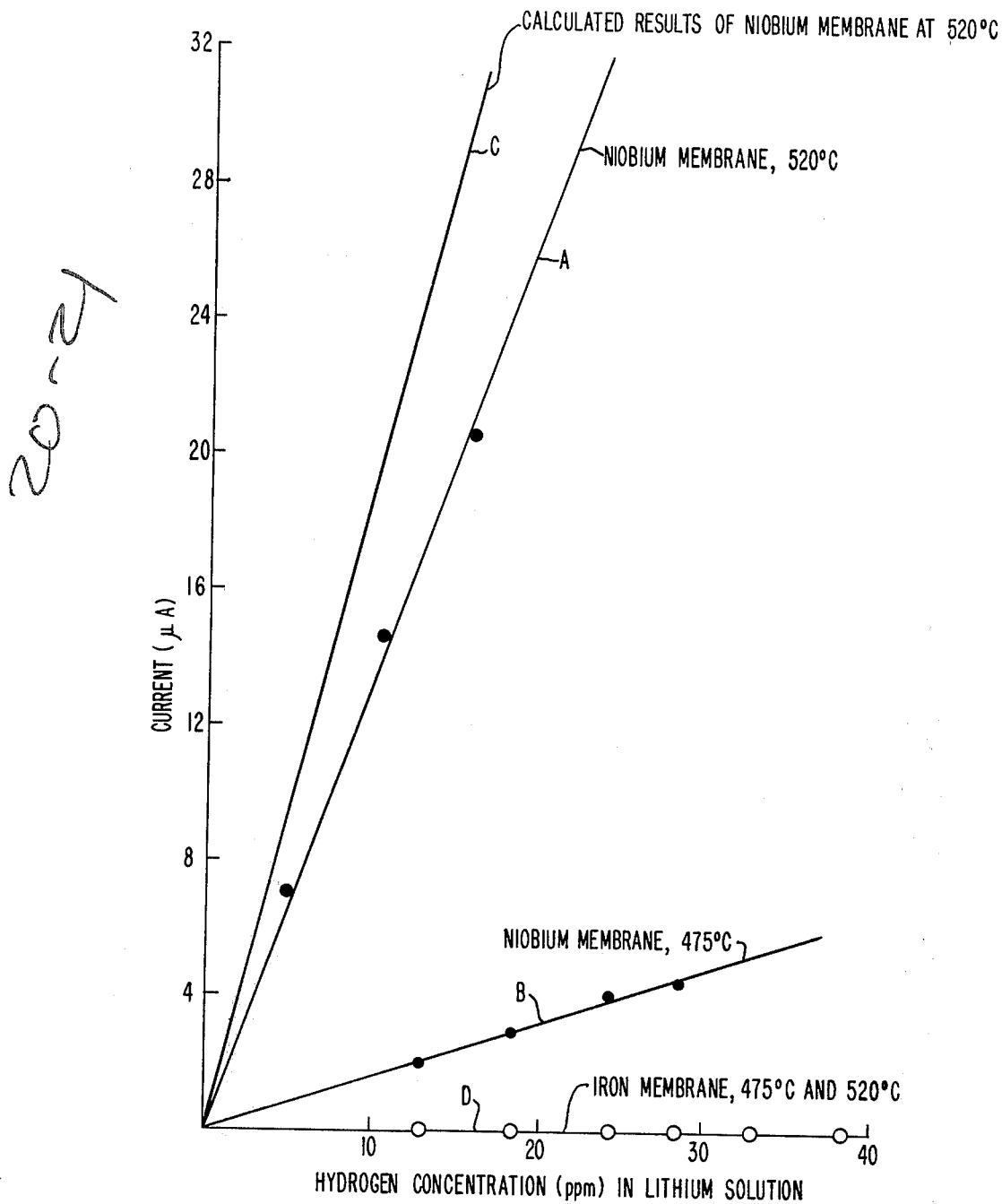
FIG. 2 is a graphical illustration of the operation of niobium and iron membranes in lithium/hydrogen solutions.

The results of experiments utilizing niobium and iron membranes in lithium/hydrogen solutions of various concentrations of hydrogen are graphically illustrated in FIG. 2. The membranes employed were closed end tubular members having a wall thickness of about 0.05 cm, and outside diameter of about 0.64 cm and a length between 3 and 5 cm. Curve A is the response of the niobium membrane operating at 520° C., while curve B is the response of a niobium membrane operating at 475° C. As is apparent from FIG. 2, the ion current is linearly dependent upon hydrogen concentration over the range of 0–28 ppm at 475° C. and 0–6 ppm at 520° C. This is in qualitative agreement with equation (1) above. The current signal at 520° C. is higher due to the temperature dependence of $K_2$ and to a lesser extent $K_1$. The membrane/meter response was quicker and the signal more stable at the higher temperatures and thus a lithium temperature of 500° C. or higher is preferred.

Curve C of FIG. 2 represents the calculated relationship between current and hydrogen concentration at 520° C. as derived from equation (1).

It has been determined experimentally that the ion pump 20 operates most effectively in a range of about 2–80 $\mu$a. The current vs. hydrogen concentration of FIG. 2 illustrates that at 520° C. sufficient flux is produced across a niobium membrane to enable even the smallest, i.e., <1 ppm, hydrogen concentration change to be monitored.

In order to demonstrate the superiority of the niobium membrane, experiments were conducted with an iron membrane at 475° C. and 520° C. using an otherwise identical meter. The response of the iron membrane is plotted as curve D of FIG. 2. As is apparent from curve D, no measurable ion pump signal was developed for hydrogen concentrations between 0 and 38 ppm.

Inasmuch as the permeation constant of vanadium is comparable to that of niobium, results comparable to that illustrated in curves A and B of FIG. 2 would be realized through the use of a vanadium membrane.

It has been determined experimentally that the permeability of niobium toward hydrogen is strongly affected by the presence of surface oxide films. These films greatly decrease the release rate of hydrogen and produce permeation coefficients as much as 8 to 10 orders of magnitude lower than expected from ideal bulk diffusion. Obviously, the presence of an oxide film in the illustrated system would seriously reduce the magnitude of the ion pump current, and consequently the hydrogen-measuring effectiveness of the system. Although such oxide films can be partially removed by high temperature vacuum treatment of the niobium, it is an important feature of this invention that any residual oxygen impurity will not prove stable in the strongly reducing environment provided by liquid lithium. An oxide film may contain any of several compounds including NbO, Nb$_2$O$_4$ and Nb$_2$O$_5$. Free energy data for equations 2–4 below indicate that all three of the above oxides for which data are available will, from thermodynamic considerations, be reduced to niobium metal in the presence of excess lithium. The free energy of formation of lithium oxide is such a large negative quantity, i.e., $-133.8$ kcal/g. atom 0, that the niobium suboxides are also expected to be unstable in such a system.

$$\alpha G = -42.8 \text{ kcal}$$

$$NbO + 2Li \rightarrow Li_2O + Nb \quad (2)$$

$$\alpha G = -358.7 \text{ kcal}$$

$$Nb_2O_4 + 8Li \rightarrow 4Li_2O + 2Nb \quad (3)$$

$$\alpha G = -245.3 \text{ kcal}$$

$$Nb_2O_5 + 10Li \rightarrow 5Li_2O + 2Nb \quad (4)$$

Therefore, liquid lithium represents an oxygen sink which will maintain an oxide-free niobium surface for the niobium membrane 10, thereby allowing hydrogen permeation consistent with bulk diffusion.

I claim:

1. Apparatus for measuring the hydrogen present in a lithium/hydrogen solution, comprising,
   a housing including an opening which permits the lithium/hydrogen solution to enter the housing,
   a diffusion member being a metal selected from the group consisting of niobium and vanadium and secured within said housing such that said metal is directly contacted by the lithium/hydrogen solution, the hydrogen in the lithium/hydrogen solution diffusing through said diffusion membrane, and
   an ion pump means connected to said housing to develop a current in response to the diffusion of hydrogen, said current being indicative of the content of hydrogen in the lithium/hydrogen solution.

2. Apparatus as claimed in claim 1 further including means for heating said lithium/hydrogen solution at the interface of the solution with said membrane to a temperature of about 500° C. or higher.

3. A method of measuring the hydrogen present in a lithium/hydrogen solution, comprising the steps of,
   contacting a surface of hydrogen diffusion membrane made of niobium or vanadium with the lithium/hydrogen solution,
   establishing a differential pressure across said membrane to support the hydrogen permeation from said solution through said membrane to the opposite surface thereof,
   heating the interface of the solution and the membrane to a temperature of at least 500° C. to enhance the hydrogen permeation through said membrane, and
   developing a current in response to said hydrogen permeation which is indicative of the hydrogen content of said lithium/hydrogen solution.

4. A method as claimed in claim 3 wherein said lithium is liquid lithium, said liquid lithium maintaining the surface of said membrane contacted by said solution oxide-free and providing hydrogen permeation that is consistent with bulk diffusion.

* * * * *